United States Patent
Sharma et al.

(10) Patent No.: US 7,149,577 B2
(45) Date of Patent: Dec. 12, 2006

(54) APPARATUS AND METHOD USING ATP RETURN CYCLE LENGTH FOR ARRHYTHMIA DISCRIMINATION

(75) Inventors: Vinod Sharma, Blaine, MN (US); Paul J. Degroot, Brooklyn Park, MN (US); Rahul Mehra, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 531 days.

(21) Appl. No.: 10/307,687

(22) Filed: Dec. 2, 2002

(65) Prior Publication Data
US 2004/0106956 A1 Jun. 3, 2004

(51) Int. Cl.
- A61N 1/362 (2006.01)
- A61N 1/38 (2006.01)
- A61N 1/39 (2006.01)

(52) U.S. Cl. .................. 607/14; 607/4; 607/9; 600/518
(58) Field of Classification Search ................ 607/4–5, 607/9, 14, 28; 600/518, 515; 128/419
See application file for complete search history.

(56) References Cited

U.S. PATENT DOCUMENTS

| | | | |
|---|---|---|---|
| 4,316,472 A | 2/1982 | Mirowski et al. | |
| 4,375,817 A | 3/1983 | Engle et al. | |
| 4,384,585 A | 5/1983 | Zipes | |
| 4,407,288 A | 10/1983 | Langer et al. | |
| 4,428,378 A | 1/1984 | Anderson et al. | |
| 4,577,633 A | 3/1986 | Berkovits et al. | |
| 4,587,970 A | 5/1986 | Holley et al. | |
| 4,727,380 A | 2/1988 | Miura et al. | |
| 4,727,877 A | 3/1988 | Kallok | |
| 4,800,883 A | 1/1989 | Winstrom | |
| 4,821,723 A | 4/1989 | Baker et al. | |
| 4,830,006 A | 5/1989 | Haluska et al. | |
| 4,865,036 A | 9/1989 | Chirife | |
| 4,880,005 A | 11/1989 | Pless et al. | |
| 4,949,719 A | 8/1990 | Pless et al. | |
| 4,953,551 A | 9/1990 | Mehra et al. | |
| 4,967,747 A | 11/1990 | Carroll et al. | |
| 5,048,521 A | 9/1991 | Pless et al. | |
| 5,074,301 A * | 12/1991 | Gill | 607/4 |
| 5,107,850 A | 4/1992 | Olive | |
| 5,161,527 A | 11/1992 | Nappholz et al. | |

(Continued)

FOREIGN PATENT DOCUMENTS

WO  WO 92/18198  10/1992

OTHER PUBLICATIONS

Olson, et al., "Onset and Stability for Ventricular Tachyarrhythmia Detection in an Implantable Pacer-Carioverter-Defibrillator", *Computers in Cardiology—IEEE Computer Society Press*, Oct. 7-10, 1986, pp. 167-170.

(Continued)

*Primary Examiner*—Robert E. Pezzuto
*Assistant Examiner*—Jessica L. Reidel
(74) *Attorney, Agent, or Firm*—Michael C. Soldner; Girma Wolde-Michael

(57) ABSTRACT

An apparatus for discriminating between cardiac events that includes an input circuit receiving signals indicative of the cardiac events, a first output circuit generating pulses in response to the received signals, and a microprocessor determining whether a signal received by the input circuit subsequent to the generated pacing pulses corresponds to a predetermined cardiac event in response to an elapsed time period between the generated pulses and the subsequently received signal and a predetermined discrimination threshold.

42 Claims, 9 Drawing Sheets

U.S. PATENT DOCUMENTS

| | | |
|---|---|---|
| 5,163,427 A | 11/1992 | Keimel |
| 5,176,137 A | 1/1993 | Erickson et al. |
| 5,184,615 A * | 2/1993 | Nappholz et al. .............. 607/14 |
| 5,188,105 A | 2/1993 | Keimel |
| 5,191,884 A | 3/1993 | Gilli et al. |
| 5,193,535 A | 3/1993 | Bardy et al. |
| 5,193,536 A | 3/1993 | Mehra |
| 5,205,583 A | 4/1993 | Henseler et al. |
| 5,209,229 A | 5/1993 | Gilli |
| 5,243,980 A * | 9/1993 | Mehra ............................ 607/6 |
| 5,251,624 A | 10/1993 | Bocek et al. |
| 5,318,591 A | 6/1994 | Causey et al. |
| 5,330,505 A | 7/1994 | Cohen |
| 5,458,619 A | 10/1995 | Olson |
| 5,545,186 A | 8/1996 | Olson et al. |
| 5,662,688 A | 9/1997 | Haefner et al. |
| 5,755,736 A | 5/1998 | Gillberg et al. |
| 5,855,893 A | 1/1999 | Weinkauf et al. |
| 5,913,550 A | 6/1999 | Watanuki |
| 5,978,707 A | 11/1999 | Krig et al. ..................... 607/14 |
| 5,991,656 A | 11/1999 | Olson et al. |
| 6,167,308 A | 12/2000 | DeGroot |
| 6,178,350 B1 | 1/2001 | Olson et al. |
| 6,330,477 B1 | 12/2001 | Casavant ...................... 607/14 |
| 6,345,199 B1 | 2/2002 | Thong ............................ 607/5 |
| 6,539,254 B1 * | 3/2003 | Kroll .............................. 607/4 |
| 2003/0023273 A1 * | 1/2003 | DeGroot et al. ................ 607/4 |
| 2004/0088017 A1 * | 5/2004 | Sharma et al. ................. 607/25 |
| 2005/0251217 A1 * | 11/2005 | Brown ......................... 607/14 |

OTHER PUBLICATIONS

Arzbaecher, et al., "Automatic Tachycardia Recognition", *PACE*, vol. 7, May-Jun. 1984, Part II, pp. 541-547.

Arenal, et al., "First Postpacing Interval Variability During Right Ventricular Stimulation", *American Heart Association*, 1998, pp. 671-677.

* cited by examiner

APPARATUS AND METHOD USING ATP RETURN CYCLE LENGTH FOR ARRHYTHMIA DISCRIMINATION

FIELD OF INVENTION

The present invention relates generally to arrhythmia discrimination in an implantable medical device (IMD), and in particular, the present invention relates to determining whether a detected tachycardia is a supraventricular tachycardia (SVT) or a ventricular tachycardia (VT) subsequent to delivery of therapy in response to a detected cardiac event and subsequently inhibiting or permitting scheduled delivery of the therapy.

BACKGROUND OF THE INVENTION

Implantable cardioverter defibrillator (ICD) art has long distinguished ventricular arrhythmias by rate and type. Ventricular tachycardias (VTs) generally are those arrhythmias with rates between 150 and 250 bpm. These rhythms can be further differentiated by their ECG configuration as either monomorphic or polymorphic. Arrhythmias with rates above the upper VT range are typically classified as Ventricular Fibrillation (VF).

To treat each type of arrhythmia in the appropriate manner, some ICDs are equipped with "tiered therapies" for delivering therapy based on the type of arrhythmia detected by the device. Devices such as ICDs, generally differentiate types of arrhythmias by rate. Less dangerous arrhythmias such as VTs may be treated by delivering a series of low-power, relatively high-rate, pacing pulses to the heart. This therapy is often referred to as anti-tachycardia pacing (ATP) therapy. For faster VTs or if ATP therapy is anticipated to be ineffective or to take too long, the device may be pre-set to deliver cardioversion shocks which typically are synchronized to R-waves. In contrast, more perilous arrhythmias such as VFs are often treated using a more aggressive shock therapy, which may not always be synchronized to a detected event.

Certain fast ventricular rates may be caused by irregularities originating in cardiac anatomical areas other than the ventricles. These are supraventricular tachycardias (SVTs) which can produce fast ventricular rates that meet the rate/duration detection methods, resulting in appropriate therapy. Therapy delivered to the ventricles is typically ineffective in treating SVTs because it may not reach the true origin of the tachycardia. These inappropriate therapies cause considerable discomfort to the patient and waste energy. As a result, accurate discrimination of SVT from VT is an important factor in assuring appropriate therapy is delivered.

Additionally, high-voltage shocks may be "over-used" to treat conditions that could otherwise be successfully treated using ATP. For example, the more aggressive treatment may be prescribed because most clinicians prefer a fast termination of the arrhythmia rather than allowing time to pass while a determination is made as to whether ATP therapy will terminate the rhythm. This tendency to utilize a more aggressive therapy is intended to reduce the possibility of patient syncope. However, this rationale results in some patients unnecessarily enduring the pain of a high-voltage shock when painless ATP therapy could have successfully terminated the rhythm, or the shock is ineffective because the tachycardia is of atrial/AV nodal origin.

Preventing the unnecessary delivery of high-voltage shocks has long been recognized as a very desirable goal. As a result, monitoring the rhythm during the charging of the high-voltage capacitors in preparation for shock delivery has been proposed. For example in U.S. Pat. No. 4,949,719, issued to Pless et al, and U.S. Pat. No. 5,191,884 issued to Gilli et al., the implanted device monitors heart rhythm during charging to determine whether the arrhythmia has spontaneously terminated, and thereafter aborts the charging of the output capacitors if the rhythm has returned to normal.

Another approach to this issue is found in U.S. Pat. No. 5,318,591, issued to Causey et al., and incorporated herein by reference in its totality. The ICD begins charging its high-powered capacitors in parallel with the application of the ATP therapy. In addition, this charging may also start in parallel with the verification interval immediately following the previous therapy, during which time the ICD attempts to verify arrhythmia termination. Numerous other patents describe ATP pacing including U.S. Pat. No. 5,193,536, issued to Mehra, U.S. Pat. No. 5,458,619 issued to Olson, U.S. Pat. No. 6,167,308, issued to DeGroot, and U.S. Pat. No. 6,178,350, issued to Olson, et al. Other patents describe in more detail systems that analyze the sequence and timing of events prior to the selection of a therapy. Such patents include U.S. Pat. No. 5,205,583 issued to Olson, U.S. Pat. No. 5,913,550 issued to Duffin, U.S. Pat. No. 5,193,535 issued to Bardy et al., U.S. Pat. No. 5,161,527 issued to Nappholz et al., U.S. Pat. No. 5,107,850 issued to Olive and U.S. Pat. No. 5,048,521, issued to Pless et al.

In the patents listed above, several basic strategies are generally followed. A first strategy is to associate each type of arrhythmia with a predetermined set of criteria. Next, a patient's heart rhythm is monitored to identify a heart event, including intervals and/or rates associated with the event. This information is then compared against the various criteria sets to analyze the likelihood that the event may be characterized as a specific type of arrhythmia. Monitoring continues until one of the criteria sets is met, resulting in detection and diagnosis of the arrhythmia. A second basic strategy involves defining a set of criteria for events, intervals, and rates that is generally indicative of a group of arrhythmias. After the criterion is met, the preceding and/or subsequent events are analyzed to determine which specific arrhythmia is present.

As is evident from a review of the above-cited references, many implantable anti-tachycardia pacemakers provide a variety of ATP regimens. Normally, these regimens are applied according to a pre-programmed sequence, such as burst or ramp therapies among others. Each therapy extends over a predetermined number of pacing pulses. After delivery of these pacing pulses, the devices generally determine whether the pulses were effective in terminating the detected arrhythmia episode as may be confirmed by a return to sinus rhythm. This is identified by detecting a sequence of spontaneous depolarizations separated by greater than a predefined interval. In the absence of detected termination, the ICD applies more aggressive therapies such as synchronized cardioversion pulses or defibrillation shocks. While the delivery of ATP in some cases makes shock therapy unnecessary, a further reduction in the delivery of high-voltage shocks is still desirable.

Certain tachycardias may originate in the atria or AV node. These supraventricular tachycardias are not amenable to termination by therapies delivered to the ventricles. Methodologies are currently employed to discriminate between SVTs and VTs and withhold or permit the scheduled therapy. What is needed, is a method and apparatus to discriminate between SVTs and VTs before or during capacitor charging to inhibit a scheduled shock therapy or permit it.

SUMMARY OF THE INVENTION

The present invention is directed to an apparatus for discriminating between cardiac events that includes an input circuit receiving signals indicative of the cardiac events, a first output circuit generating pulses in response to the received signals, and a microprocessor determining whether a signal received by the input circuit subsequent to the generated pacing pulses corresponds to a predetermined cardiac event in response to an elapsed time period between the generated pulses and the subsequently received signal and a predetermined discrimination threshold.

According to an embodiment of the present invention, an apparatus for discriminating between cardiac events includes an input circuit receiving signals indicative of the cardiac events, and a first output circuit generating pulses in response to the input circuit receiving consecutive signals, separated by a predetermined time period, corresponding to the rate of a first predetermined cardiac event. A microprocessor determines whether a signal received by the input circuit subsequent to the generated pacing pulses corresponds to the first predetermined cardiac event in response to an elapsed time period between the generated pulses and the subsequently received signal and a predetermined discrimination threshold.

According to yet another embodiment of the present invention, a method of discriminating between cardiac events includes receiving signals indicative of the cardiac events, generating pulses in response to the received signals, and determining that a signal received by the input circuit subsequent to the generated pacing pulses corresponds to a first predetermined cardiac event in response to an elapsed time period (T3) between the generated pulses and the subsequently received signal and a predetermined discrimination threshold (T4).

DETAILED DESCRIPTION OF THE INVENTION

The present invention relates to an apparatus and method for determining whether a detected tachyarrhythmia is supraventricular tachycardia (SVT) or ventricular tachycardia (VT). Principally, antitachycardia pacing pulses are delivered, and after the last pulse, the system monitors the time before an intrinsic heart beat is sensed. If the time it took to sense the intrinsic heart beat is longer than a predetermined time window, the system classifies the tachycardia as an SVT. This conclusion is made on the reliance that because the antitachycardia pulses would normally result in the AV node being in a refractory condition, an impulse from the atrium will not make it through the ventricle right away. Whereas, if the impulse started in the ventricle, implying the possibility of a ventricular tachycardia, an intrinsic heart beat would be sensed sooner because the pulse does not have to travel through the refractory AV node.

The present invention provides various embodiments and implementations thereof. In one preferred embodiment, pacing pulses are delivered while the capacitor is charging to deliver a shock. Other embodiments implement delivery of pacing pulses before capacitors start to charge. Further, other embodiments include implantable medical devices that integrate drug delivery therapy. The present invention, in cooperation with such systems, could be used to determine whether the tachyarrhythmia is an SVT or VT to thereby provide appropriate drug therapy.

Figure 1:
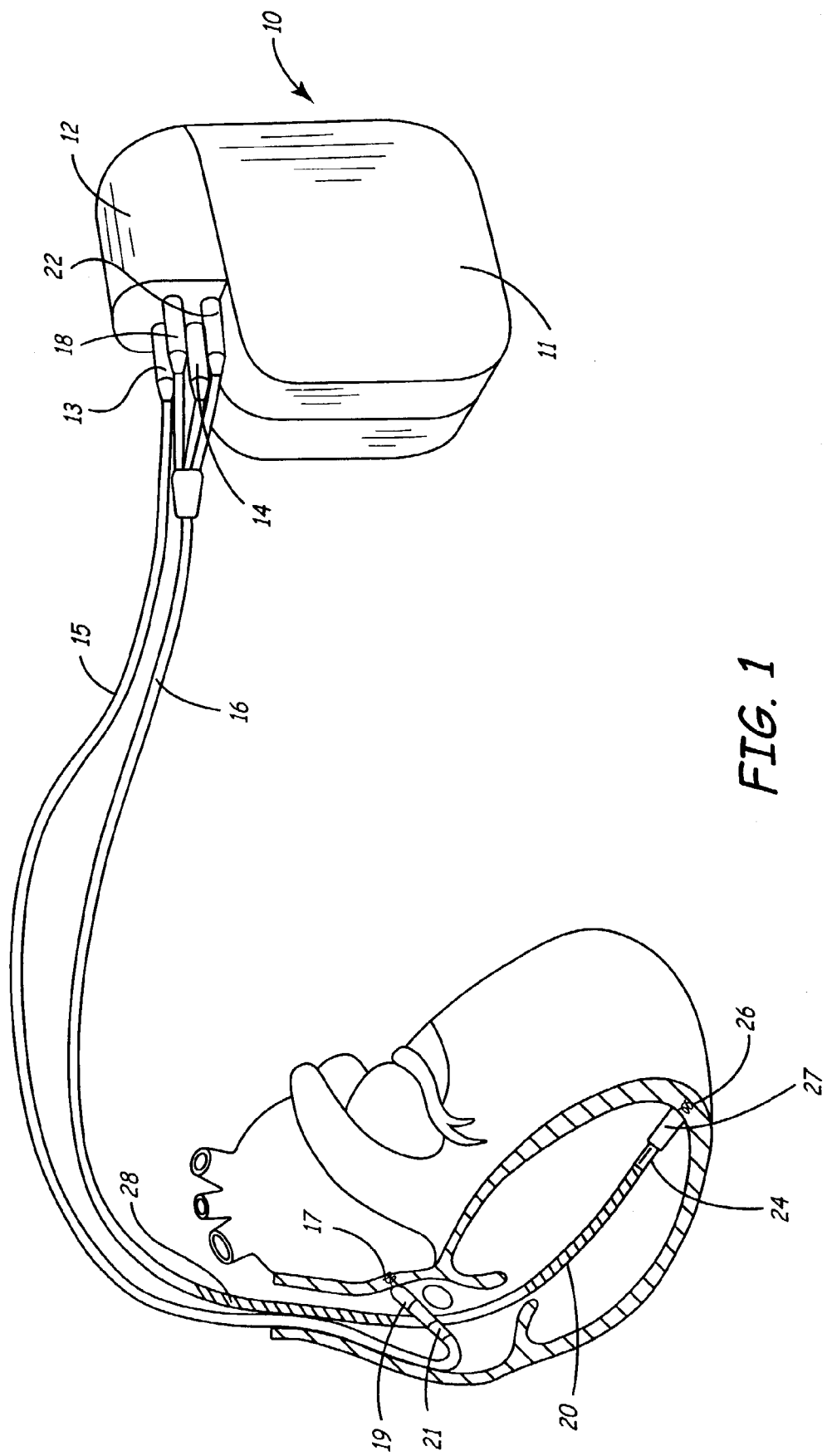
FIG. 1 is a schematic diagram of a transvenous electrode system in conjunction with a pacemaker/cardioverter/defibrillator in which the present invention may be embodied.

FIG. 1 illustrates one embodiment of a pacemaker/cardioverter/defibrillator device 10 and lead set in which the present invention may be usefully practiced. The example embodiment is Illustrated and described as a dual chamber implantable cardioverter defibrillator (ICD). Alternatively, the present invention may be embodied in other implantable medical devices (IMDs), such as single chamber ICDs, pacemakers, drug pumps, and nerve stimulators. In the exemplary ICD of FIG. 1 the ventricular lead includes an elongated insulative lead body 16, carrying four mutually insulated conductors, including a ring electrode 24, an extendable helix electrode 26, mounted retractably within an insulative electrode head 27, and elongated coil electrodes 20 and 28. Each of the electrodes is coupled to one of the coiled conductors (not shown) within the lead body 16. Electrodes 24 and 26 are employed for cardiac pacing and for sensing ventricular depolarizations. Electrodes 20 and 28 are employed in conjunction with the conductive housing 11 of the pacemaker/cardioverter/defibrillator 10 for delivery of cardioversion and defibrillation pulses. At the proximal end of the lead body 16 are two unipolar connectors 18 and 22 which each carry a connector pin (not shown) coupled to one of the coiled electrodes 20 and 28. Electrical connector 14 is an in-line bipolar connector carrying a connector ring and a connector pin (not shown), coupled to electrodes 24 and 26, respectively.

The atrial lead as illustrated is a conventional bipolar atrial pacing lead. The atrial lead includes an elongated insulative lead body 15, carrying two concentric coiled conductors (not shown), separated from one another by tubular insulative sheaths. Located adjacent the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. At the proximal end of the lead is an in-line connector 13 which carries a connector ring and a connector pin (not shown), coupled to electrodes 21 and 17, respectively. In alternative lead systems, a defibrillation electrode, for example corresponding to electrode 28, might instead be mounted to the atrial lead, or might be mounted to a coronary sinus lead, for location in the coronary sinus and great cardiac vein.

An implantable pacemaker/cardioverter/defibrillator 10 is shown in combination with the leads, with the lead connectors 13, 14, 18 and 22 inserted into the connector block 12, which contains corresponding electrical connectors for coupling to the various connector rings and pins. Optionally, insulation of the outward facing portion of the housing 11 of the pacemaker/cardioverter/defibrillator 10 may be provided in the form of a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 serves as a subcutaneous defibrillation electrode, used in conjunction with one or both of electrodes 20 and 28.

Figure 2:
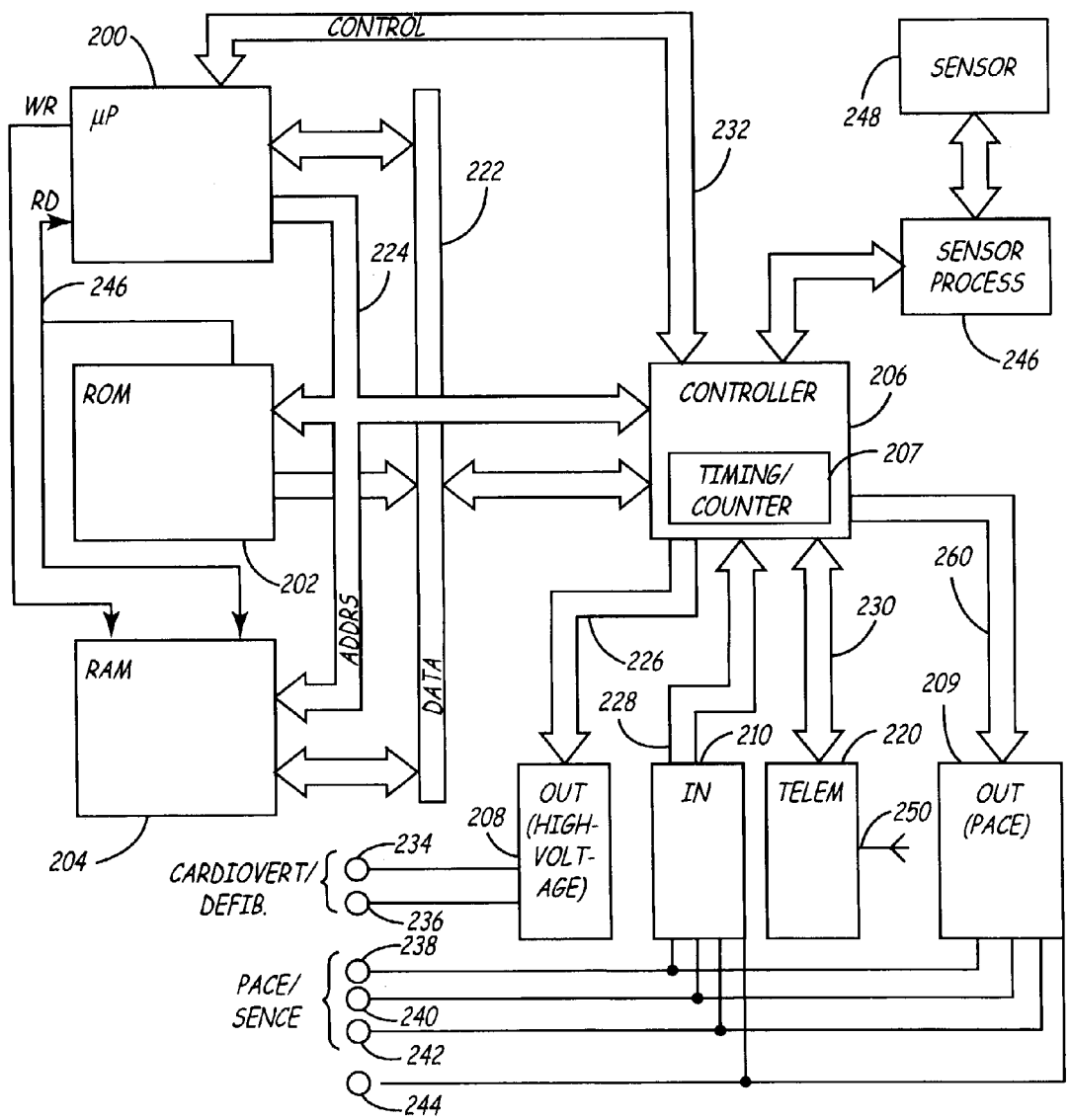
FIG. 2 is a block functional diagram illustrating the structure of one embodiment of an implantable pacemaker/cardioverter/defibrillator in which the present invention may be embodied.

FIG. 2 is a functional block diagram of an implantable pacemaker/cardioverter/defibrillator (ICD) in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

As illustrated in FIG. 2, the device is embodied as a microprocessor based stimulator. However, other digital and/or analog circuit embodiments are possible within the scope of the invention. For example, devices having general structures as illustrated in U.S. Pat. No. 5,251,624 issued to Bocek et al., U.S. Pat. No. 5,209,229 issued to Gilli, U.S. Pat. No. 4,407,288, issued to Langer et al, U.S. Pat. No. 5,662,688, issued to Haefner et al., U.S. Pat. No. 5,855,893, issued to Olson et al., U.S. Pat. No. 4,821,723, issued to Baker et al. or U.S. Pat. No. 4,967,747, issued to Carroll et al., all incorporated herein by reference in their entireties, may also be usefully employed in conjunction with the present invention. FIG. 2 should be considered illustrative, rather than limiting with regard to the scope of the invention.

The primary elements of the apparatus illustrated in FIG. 2 are a microprocessor 200, read-only memory (ROM) 202, random-access memory (RAM) 204, a digital controller 206, an input amplifier circuit 210, two output circuits 208 and 209, and a telemetry/programming unit 220. Read-only memory 202 stores the basic programmed instructions to be executed by microprocessor 200, and may further store parameters to define the various timing intervals employed by the ICD. RAM 204 generally stores data and variable control parameters, such as programmed pacing rate, programmed cardioversion and defibrillation energy, pulse widths, pulse amplitudes, and so forth that may be programmed into the device by the physician. Random-access memory 204 also stores derived values, such as the stored time intervals separating tachyarrhythmia pulses and the corresponding high-rate pacing interval.

Controller 206 performs all of the basic control and timing functions of the device. Controller 206 includes at least one programmable timing counter 207, which is initiated upon detection of a ventricular depolarization, and which times intervals thereafter. This counter 207 is used to generate the basic timing intervals used to deliver anti-tachycardia pacing (ATP) pulses, and to measure other intervals used within the context of the current invention. On time-out of the pacing escape interval or in response to a determination that a cardioversion or defibrillation pulse is to be delivered, controller 206 triggers charging of output circuit 208 so that the appropriate shock waveform may be delivered, as discussed below.

Following generation of stimulus pulses, controller 206 may be utilized to generate corresponding interrupts on control bus 232, causing microprocessor 200 to perform any required mathematical calculations and other operations associated with selection of anti-tachyarrhythmia therapies according to the present invention. A timing/counter circuit in controller 206 may also control timing intervals such as ventricular refractory periods, as is known in the art based on parameters stored in RAM 204 or ROM 202.

Controller 106 may also generate interrupts to microprocessor 200 on the occurrence of sensed ventricular beats. In addition, controller 206 may provide a timer value on data bus 222 to be used by microprocessor 200 in determining whether a tachyarrhythmia is present. This circuit may also be used to measure cardiac cycle lengths within the context of the current invention.

Output stage 208 contains a high-output pulse generator capable of generating cardioversion pulses of at least 0.1 joules, to be applied to the patient's heart. Typically the high output pulse generator includes one or more high-voltage capacitors, a charging circuit, and a set of switches to allow delivery of monophasic or biphasic cardioversion or defibrillation pulses via electrodes 234 and 236. The electrodes typically are large surface area electrodes mounted subcutaneously, or on or in the heart. Other electrode configurations may also be used, including two or more electrodes arranged within and around the heart.

In addition to output circuit 208, output circuit 209 is provided to generate pacing pulses. This circuit contains a pacing pulse generator circuit that is coupled to electrodes 238, 240, 242, and 244, and which are employed to accomplish cardiac pacing, including ATP pacing pulses, by delivery of a electrical stimulation between electrode pairs 238 and 240, and 242 and 244. Electrode 238 is typically located on the distal end of an endocardial lead, and is typically placed in the apex of the right ventricle. Electrode 240 may be a ring electrode located on an endocardial lead slightly proximal to the tip electrode 238. Electrode 242 is typically located on the distal end of an endocardial lead, and is typically placed in the right atrium. Electrode 244 may be a ring electrode located on an endocardial lead slightly proximal to the tip electrode 242. Output circuit 209 is controlled by controller 206 via control bus 226. Controller 206 determines the time, amplitude and pulse width of the pulses to be delivered, and may also determine which electrode pair will be employed to deliver the pulses. Input amplifier 210 receives cardiac signals on a selected pair of electrodes 238 and 240, and 242 and 244. Signals indicating both the occurrence of intrinsic and paced atrial and ventricular events are provided to the controller 206 via bus 228. In one embodiment, controller 206 provides an interrupt to microprocessor 200 via control bus 232 following a detected beat, allowing the microprocessor to perform any necessary calculations or to update values stored in RAM 204.

In one embodiment, one or more physiologic sensors 248 are included in the system. For example, sensor(s) 248 may include a hemodynamic sensor such as an impedance sensor as disclosed in U.S. Pat. No. 4,865,036, issued to Chirife, or a pressure sensor as disclosed in U.S. Pat. No. 5,330,505, issued to Cohen, both of which are incorporated herein by reference in their entireties. Alternatively, sensor 248 may be a demand sensor for measuring cardiac output parameters, such as an oxygen saturation sensor disclosed in U.S. Pat. No. 5,176,137, issued to Erickson et al, or a physical activity sensor as disclosed in U.S. Pat. No. 4,428,378, issued to Anderson et al, both of which are incorporated herein by reference in their entireties. Sensor processing circuitry 246 transforms the sensor output into digitized values for use in conjunction with detection and treatment of arrhythmias.

External control of the implanted pacemaker/cardioverter/defibrillator is accomplished via telemetry/control block 220 that controls communication between the implanted pacemaker/cardioverter/defibrillator and an external programmer. Any conventional programming/telemetry circuitry is believed workable in the context of the present invention. Information entering the pacemaker/cardioverter/defibrillator from the programmer is passed to controller 206 via bus 230. Similarly, information from the pacemaker/cardioverter/defibrillator is provided to the telemetry block 220 via bus 230.

A portion of the memory 204 may be configured as a plurality of recirculating buffers, capable of holding series of measured intervals, which may be analyzed in response to the occurrence of a pace or sense interrupt to determine whether the patient's heart is presently exhibiting an atrial or ventricular tachyarrhythmia. The arrhythmia detection method of the present invention may include prior art tachyarrhythmia detection algorithms. The entire ventricular arrhythmia detection methodology of presently available Medtronic pacemaker/cardioverter/defibrillators may be employed as part of the arrhythmia detection and classification method according to the disclosed preferred embodiment of the invention. However, any of the various arrhythmia detection methodologies known to the art might also usefully be employed in alternative embodiments of the invention. In the event that an atrial or ventricular tachycardia is detected, and an anti-tachyarrhythmia pacing regimen is desired, appropriate timing intervals for controlling generation of anti-tachyarrhythmia pacing therapies are loaded from microprocessor 200 into the pacer timing and control circuitry 209, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in U.S. Pat. No. 4,577,633, issued to Berkovits et al on Mar. 25, 1986. U.S. Pat. No. 4,880,005, issued to Hess et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In response to the detection of atrial or ventricular fibrillation or tachyarrhythmia requiring a cardioversion or defibrillation pulse, microprocessor 200 activates cardioversion/defibrillation control circuitry 208, which initiates charging of the high voltage capacitors. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Patent Application No. WO92/18198 by Adams et al, published Oct. 29, 1992, and in U.S. Pat. No. 4,316,472 by Mirowski et al, issued Feb. 23, 1982, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, delivery of the cardioversion or defibrillation pulses is accomplished by output circuit 208, under control of control circuitry 206 via control bus 226. Output circuit 208 determines whether a monophasic or biphasic pulse is delivered. An example of output circuitry for delivery of biphasic pulse regimens may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable implantable/cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer or no attempts at anti-tachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that fibrillation is identified, the typical therapy will be delivery of a high amplitude defibrillation pulse, typically in excess of 5 joules. Lower energy levels may be employed for cardioversion. As in the case of currently available implantable pacemaker/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al, U.S. Pat. No. 4,727,380, issued to Vollmann et al, and U.S. Pat. No. 4,587,970, issued to Holley et al.

The above described scheme for detection and treatment of tachyarrhythmia should be considered exemplary of illustrating the invention. Other tachyarrhythmia detection methodologies, including detection methods as described in U.S. Pat. No. 5,991,656, issued to Olson, et al. on Nov. 23, 1999, U.S. Pat. No. 5,755,736, issued to Gillberg, et al. on May 26, 1998, both incorporated herein by reference in their entireties, or other known tachyarrhythmia detection methods may be substituted. It is believed that the discrimination methods of the present invention may be usefully practiced in conjunction with virtually any underlying atrial or ventricular tachyarrhythmia detection scheme. Other exemplary detection schemes are described in U.S. Pat. No. 4,726,380, issued to Vollmann, U.S. Pat. No. 4,880,005, issued to Pless et al. and U.S. Pat. No. 4,830,006, issued to Haluska et al., incorporated by reference in their entireties herein. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology* Oct. 7–10, 1986, IEEE Computer Society Press, pages 167–170, also incorporated by reference in its entirety herein. However, other criteria may also be measured and employed in conjunction with the present invention.

The following exemplary VT/VF detection method corresponds to that employed in commercially marketed Medtronic implantable pacemaker/cardioverter/defibrillators and employs rate/interval based timing criteria as a basic mechanism for detecting the presence of a tachyarrhythmia. To this end, the device defines a set of rate ranges and associated software-defined counters to track the numbers of intervals falling within the defined ranges.

A first rate range may define a maximum R-R interval used for fibrillation detection. This interval combined with the ventricular sense blanking period defines the ventricular fibrillation detection zone. The associated VF count preferably indicates how many of a first predetermined number of the preceding R-R intervals were less than the maximum fibrillation interval.

A second rate range may include R-R intervals less than a maximum ventricular tachycardia interval but greater than the maximum fibrillation detection interval. These intervals define the VT detection zone. The associated VT count is incremented in response to an R-R interval with this zone.

Optionally, the device may include a third rate range including R-R intervals greater than the maximum VF interval but less than the shortest VT interval. These intervals define the fast ventricular tachycardia (FVT) detection zone. The associated count for R-R intervals in the FVT detection zone may employ counters from the other zones and a method to differentiate FVT from VT and VF.

For purposes of the present invention, the particular details of implementation of the rate/interval based detection methodologies are not of primary importance. However, it is required that the rate based detection methodologies employed by the device allow identification and detection of rhythms in the rate range in which operation of the discrimination function is desired. Diagnosis of the detected arrhythmia and a selection of the therapy to be delivered can likewise be pre-set to occur in response to the rate/interval and duration based criteria only being met.

The present invention may be included in the exemplary ICD along with a prioritized rule base method for diagnostic and treatment of an arrhythmia as described in U.S. Pat. No. 5,545,186 issued to Olson et al on Aug. 13, 1996 incorporated herein by reference in its entirety. The device disclosed in the aforementioned patent employs a method of arrhythmia classification based on a set of prioritized rules. Some rules, when met, trigger delivery of antiarrhythmia therapy. Other rules, when met, inhibit delivery of antiarrhythmia therapy. The highest priority rule governs the behavior of the device.

Included in the behavior of the prioritized rule classification is the withholding of ventricular therapy when specific SVTs are identified, such as sinus tachycardia, atrial flutter/fibrillation, and AV nodal reentry tachycardia. Rule based detection is typically employed only during initial detection of an episode, whereas the current invention may also be applied to redetection of the ongoing episode after the previous therapy has failed.

Figure 3A:
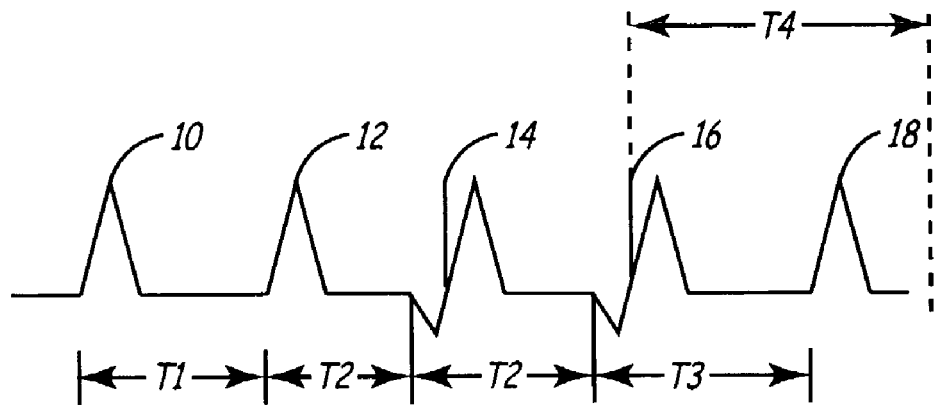
FIGS. 3a and 3b are simulated ECG strips illustrating an embodiment of the return-cycle-length-based discrimination according to the present invention.
Figure 3B:
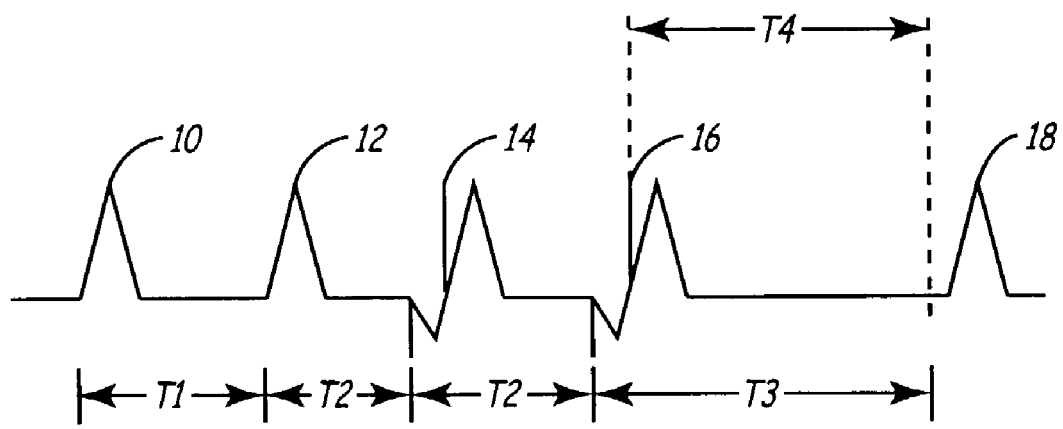

Timing diagrams FIGS. 3A and 3B depict simulated electrocardiograms (ECGs) showing a method for distinguishing between an ongoing ventricular tachycardia (VT) and an ongoing supraventricular tachycardia (SVT) according to the present invention.

In FIG. 3A cardiac depolarization pulses 10 and 12 are indicative of an ongoing cardiac event, such as a ventricular tachycardia or a supraventricular tachycardia, for example, for which treatment options are available, occurring just prior to detection, such as separated by interval T1 corresponding to the rate of the cardiac event. After the detection of cardiac depolarizations 10 and 12 indicating the presence of a tachyarrhythmia, a series of antitachycardia pacing (ATP) pulses 14 and 16 are delivered separated by intervals T2. Intervals T2 are determined as a function of the length of interval T1 and are typically a smaller percentage of interval T1.

Once delivery of ATP pulses 14 and 16 has been completed, the device notes the time elapsed since delivery of ATP pulses has been completed. For example, the device determines an elapsed time interval T3 between the last delivered pulse 16 and sensing of a subsequently received pulse 18 corresponding to an intrinsic cardiac event occurring after delivery of pulses 14 and 16. This elapsed time interval T3, which is referred to as the Return Cycle Length (RCL), is compared to a cutoff or discrimination threshold interval T4 to provide an indication of whether the tachyarrhythmia is a predetermined cardiac event, such as an SVT or a VT for example. The physiological basis of this concept is that wavefronts initiated by the ATP pulses can retrogradely penetrate the AV node, causing the AV node to be relatively refractory. When ATP is stopped, an impulse originating above the ventricles will be delayed when attempting to conduct antegradely to the ventricles. In contrast, such is not the case for an intrinsic impulse originating in the ventricles because the AV node is not involved in the conduction pathway from the locus of the impulse to the sensing lead.

According to the present invention, discrimination threshold interval T4 is a percentage of the rate of pulses 10 and 12 indicative of the detected cardiac event, i.e., the length of interval T1. For example, according to one embodiment of the present invention, discrimination threshold T4 is equal to 190% of interval T1. In this way, as illustrated in FIG. 3A, when the return cycle length, corresponding to the last pulse 16 of the delivered pulses 14 and 16 and subsequently received pulse 18, is less than discrimination threshold T4, subsequently received pulse 18 is determined to correspond to the detected ongoing cardiac event that was previously indicated by pulses 10 and 12, and therefore further treatment such as additional pacing, pacing at an increased rate or level, or shock therapy is performed. For example, if the detected ongoing cardiac event that was previously indicated by pulses 10 and 12 corresponds to a VT event, subsequently received pulse 18 is determined to correspond to a VT event.

On the other hand, as illustrated in FIG. 3B, when the return cycle length corresponding to the last pulse 16 of the delivered pulses 14 and 16 and subsequently received pulse 18 is determined to be greater than or equal to discrimination threshold T4, subsequently received pulse 18 is determined not to correspond to the ongoing cardiac event that was previously indicated by pulses 10 and 12, and therefore therapy for treating the detected ongoing cardiac event is inhibited. For example, if the ongoing cardiac event that was previously indicated by pulses 10 and 12 corresponds to a VT event, subsequently received pulse 18 is determined to not correspond to a VT event and is classified as being a SVT event, and various actions may be initiated depending on the ICD system implanted, as described below.

It is understood that the number of depolarization pulses and ATP pulses is not intended to be limited in any way and may include any number of pulses other than two and three, respectively, as described above, and that two depolarization pulses and three ATP pulses are used for brevity sake.

According to an embodiment of the present invention, in order to account for variations in tachyarrhythmia cycle length, interval T3 (i.e. RCL) is normalized to the tachyarrhythmia cycle length, i.e., interval T1. The resulting fraction, termed as Normalized Return Cycle Length ($RCL_N$), is then expressed as a percentage, i.e.

$$RCL_N = \frac{(RCL)^x}{(\text{episode } CL)^y} \times 100$$

where x is equal to any integer, y is equal to a whole number, and the episode CL corresponds to the cycle length of the episode, detected from pulses 10 and 12, that was treated with pacing pulses 14 and 16, and may include a true ventricular tachycardia cycle length or a supraventricular tachycardia cycle length inappropriately detected as being a ventricular tachycardia, for example. Furthermore, episode CL may represent just one cycle of the episode or an average of several tachycardia cycles.

As an example of the above equation, when x=y=1, $$RCL_N = \frac{RCL}{(\text{episode } CL)} \times 100$$

so that, using the intervals shown in FIGS. 3A and 3B, for example, $RCL_N=(T3/T1)\times 100$ for the cardiac events shown in FIGS. 3A and 3B.

According to the present invention, when interval T3 is normalized in this way, a determination as to whether subsequently received pulse signal 18 is a predetermined cardiac event, such as an SVT event inappropriately detected as a VT event, or a true VT episode, is made using an established return cycle length cut-off value $RCL_C$ of the normalized return cycle length $RCL_N$, equivalent to interval T4 shown in FIGS. 3A and 3B. If the normalized return cycle length $RCL_N$ is determined to be greater than or equal to return cycle length cut-off value $RCL_C$, subsequently received pulse 18 is determined to correspond to the ongoing cardiac event that was previously indicated by pulses 10 and 12, and therefore further treatment for the ongoing cardiac event, such as additional pacing, pacing at an increased rate or level, or shock therapy is performed. For example, if the ongoing cardiac event that was previously indicated by pulses 10 and 12 corresponds to a VT event, subsequently received pulse 18 is determined to correspond to a VT event.

On the other hand, if the normalized return cycle length $RCL_N$ is less than the return cycle length cut-off value $RCL_C$, subsequently received pulse 18 is determined to not correspond to the ongoing cardiac event that was previously indicated by pulses 10 and 12, and therefore further treatment for the ongoing cardiac event is inhibited. For example, if the ongoing cardiac event that was previously indicated by pulses 10 and 12 corresponds to a VT event, subsequently received pulse 18 is determined to not correspond to a VT event and is classified as being a SVT event, and various actions may be initiated depending on the ICD system implanted, as described below.

According to the present invention, using the exemplary discrimination threshold (i.e. $RCL_C$) of approximately 190%, when $RCL_N$ (i.e., (T3/T1)×100) is less than 190%, the subsequently received pulse signal 18 is classified as a predetermined event, such as a VT or SVT. Further, if the $RCL_N$ is greater than 190% the tachycardia is classified as an SVT event. Note that since $RCL_N$ is a function of the tachyarrhythmia cycle length T1, the absolute cut-off value for RCL in ms is given by ($RCL_C \times T1$) and is shorter for a faster tachyarrhythmia and longer for a slower tachyarrhythmia.

It is understood that while the discrimination threshold, i.e., interval T4 in the non-normalized embodiment and $RCL_C$ in the normalized embodiment, is described as being a percentage of interval T1, the present invention is not intended to be limited to the use of a single percentage for the discrimination threshold. For example, the discrimination threshold could vary depending upon the cycle length of interval T1, or could be a continuous function of the type of cardiac event or some other variable. For example, the discrimination threshold could be a first percentage, i.e., 190%, for a cycle length less than or equal to 240 ms and a second percentage, i.e., 200% for a cycle length between 240 ms and 300 ms, and so forth. In another embodiment, the discrimination threshold, or return cycle length cut-off value $RCL_C$, is equal to 190% (320 ms/episode CL in ms) or $RCL_C$ is equal to 190% (episode CL in ms/360 ms), so that $RCL_C$ changes as a function of episode CL in both cases. For the first example the return cycle length cut-off value $RCL_C$ decreases with episode CL and is equal to 190% at CL=320 ms, and for the second example the return cycle length cut-off value $RCL_C$ increases with episode CL and is equal to 190% at CL=360 ms.

Figure 4:
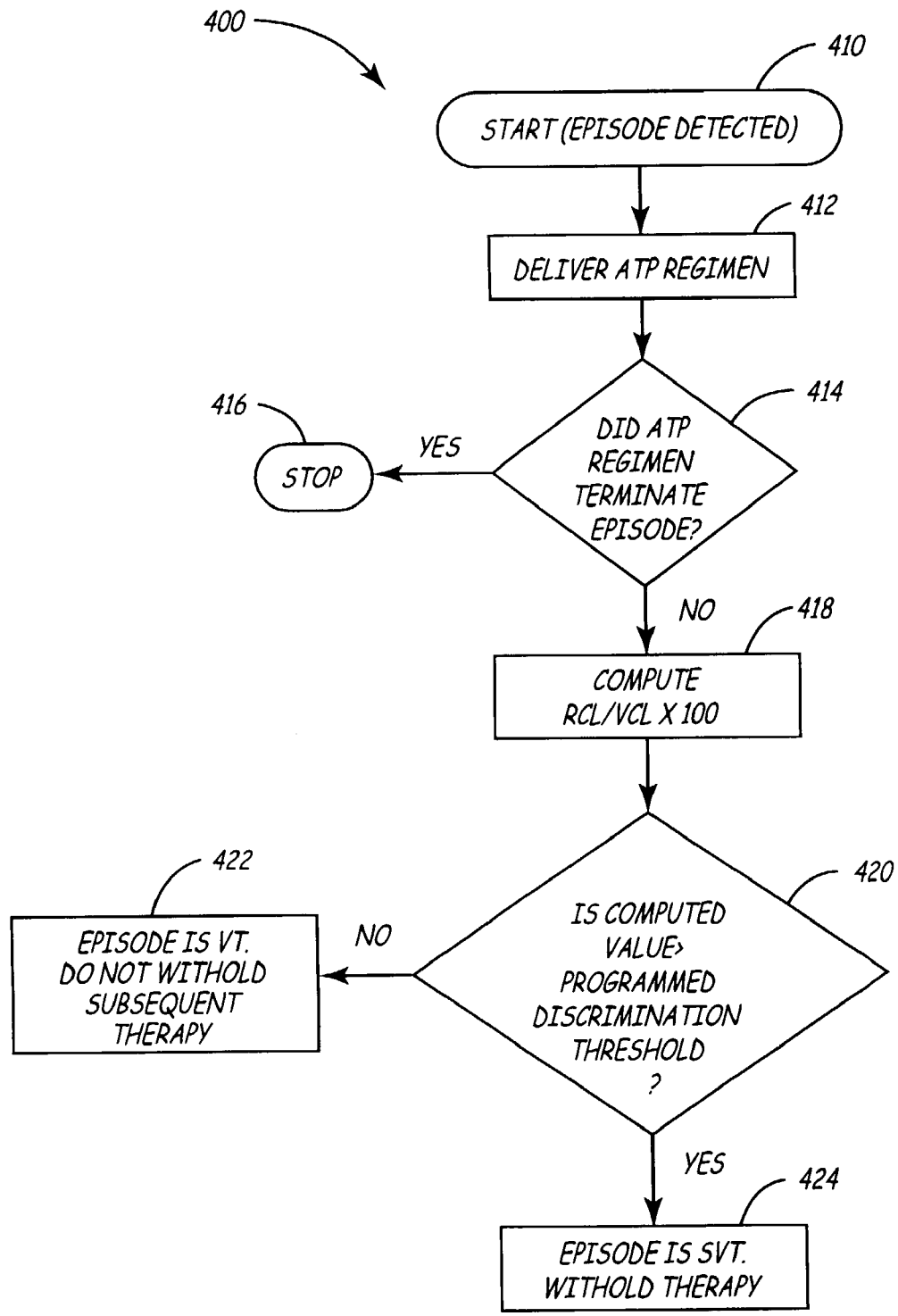
FIG. 4 is a flow chart illustrating operation of an implantable medical device (IMD) to discriminate between the presence of a supraventricular tachycardia (SVT) or ventricular tachycardia (VT) in according to an embodiment of the present invention.

Referring to FIG. 4, the functional operation of a method for discrimination of arrhythmias according to the present invention is represented in logic flow chart 400. As illustrated in FIG. 4, a method for discriminating between arrhythmias according to the present invention is initiated at logic step 410 when tachyarrhythmia episode detection occurs. In response to detecting a predetermined cardiac event, such as a VT event, for example, a series of ATP pulses are delivered, step 412. After ATP pulses are delivered, a determination is made as to whether the series of ATP pulses successfully terminated the tachyarrhythmia, step 414. If the ATP pulses are successful in terminating the tachycardia, YES in step 414, the process ends until the next detected episode, step 416. Alternatively, if the tachycardia was not terminated, NO in step 414, the normalized return cycle length ($RCL_N$) is computed, step 418, as described above, and a determination is made as to whether the computed normalized return cycle length $RCL_N$ is greater than or less than discrimination threshold interval $RCL_C$.

As described above, according to an embodiment of the present invention, if the normalized return cycle length $RCL_N$ is less than the discrimination threshold $RCL_C$, the tachycardia is classified as VT and scheduled therapy is not withheld, i.e., the scheduled therapy is delivered. If interval $RCL_N$ is greater than or equal to discrimination threshold $RCL_C$, the tachycardia is classified as SVT and subsequent ventricular therapy is withheld.

Flow chart 400 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern implantable anti-tachycardia pacemaker or implantable cardioverter defibrillator (ICD), given the disclosure herein, is well within the abilities of one of skill in the art.

According to one embodiment, the present invention may operate during the ATP During Capacitor Charging (ATP-DCC) mode of an exemplary ICD as described in commonly assigned U.S. patent application Ser. No. 10/137,517 to Ousdigian et al., entitled "COMBINED ANTI-TACHYCARDIA PACING (ATP) AND HIGH VOLTAGE THERAPY FOR TREATING VENTRICULAR ARRHYTHMIAS", filed Apr. 30, 2002, incorporated herein by reference in its entirety. In this mode an SVT/VT discrimination methodology similar to the one described in this invention that uses very short time for decision making is very well suited. The following descriptions of FIGS. 5 through 8 illustrate operation of the present invention within this embodiment.

Figure 5:
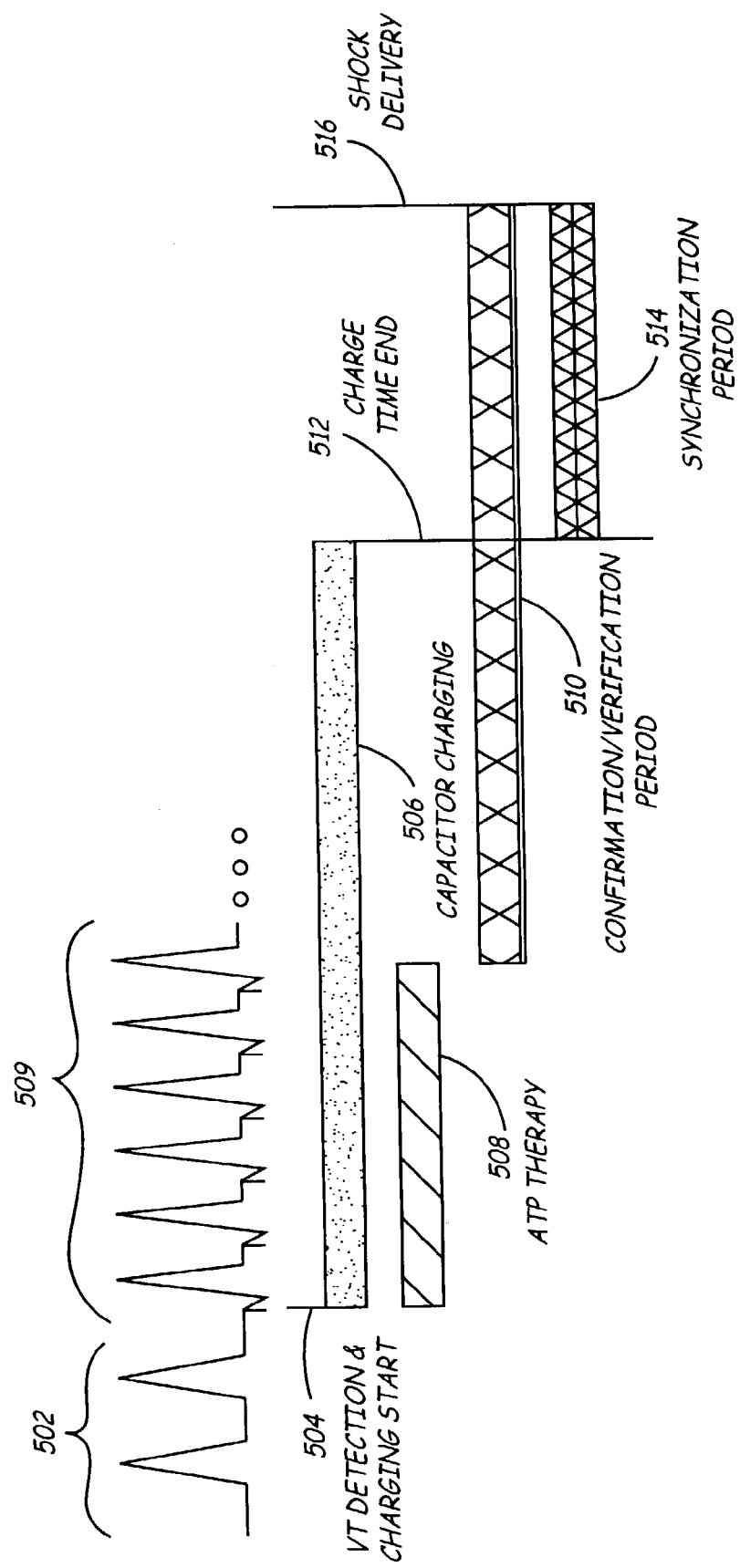
FIG. 5 is a simulated ECG strip along with timing periods illustrating an embodiment of the ATP During Capacitor Charge mode of operation, according to the present invention.

FIG. 5 is a simulated ECG illustrating a ventricular tachyarrhythmia and various timing periods to which the present invention is being applied. As illustrated in FIG. 5, pulses 502 corresponding to detection of a ventricular tachyarrhythmia start and continue for an unspecified duration of time. A device such as the exemplary ICD discussed above in reference to FIGS. 1 and 2 detects pulses 502 indicating the ventricular tachyarrhythmia at detection time 504. When the pre-set therapy is a high energy shock, ventricular tachyarrhythmia detection at time 504 starts charging of a high-energy capacitor. Charging continues during capacitor charging time period 506. Delivery of ATP pulses 509 may be initiated immediately at time 504 or sometime thereafter, and continue during an ATP therapy time period 508.

After completion of the ATP therapy time period 508, the ICD initiates a confirmation/verification time period 510 while also waiting for the next intrinsic cardiac event to be sensed. During the confirmation/verification period 510, the ICD device determines whether the ATP regimen successfully terminated the tachyarrhythmia. This determination may be made based on detecting a ventricular rate below the programmed pre-determined rate, and/or by using additional waveform morphology criteria. The confirmation/verification process corresponding to time period 510 may be performed on a beat-by-beat basis, and generally is terminated when arrhythmia termination is detected or sometime thereafter. If the arrhythmia does not terminate, period 510 may culminate in shock delivery at a shock delivery time 516 unless shock delivery is inhibited by operation of the present invention. Variations on the length of time to shock and constraints on the number of ATP pulses delivered by the exemplary ICD are described in commonly assigned U.S. patent application Ser. No. 10/137,517 to Ousdigian et al., entitled "COMBINED ANTI-TACHYCARDIA PACING (ATP) AND HIGH VOLTAGE THERAPY FOR TREATING VENTRICULAR ARRHYTHMIAS", filed Apr. 30, 2002 referenced and incorporated herein above.

Figure 6:
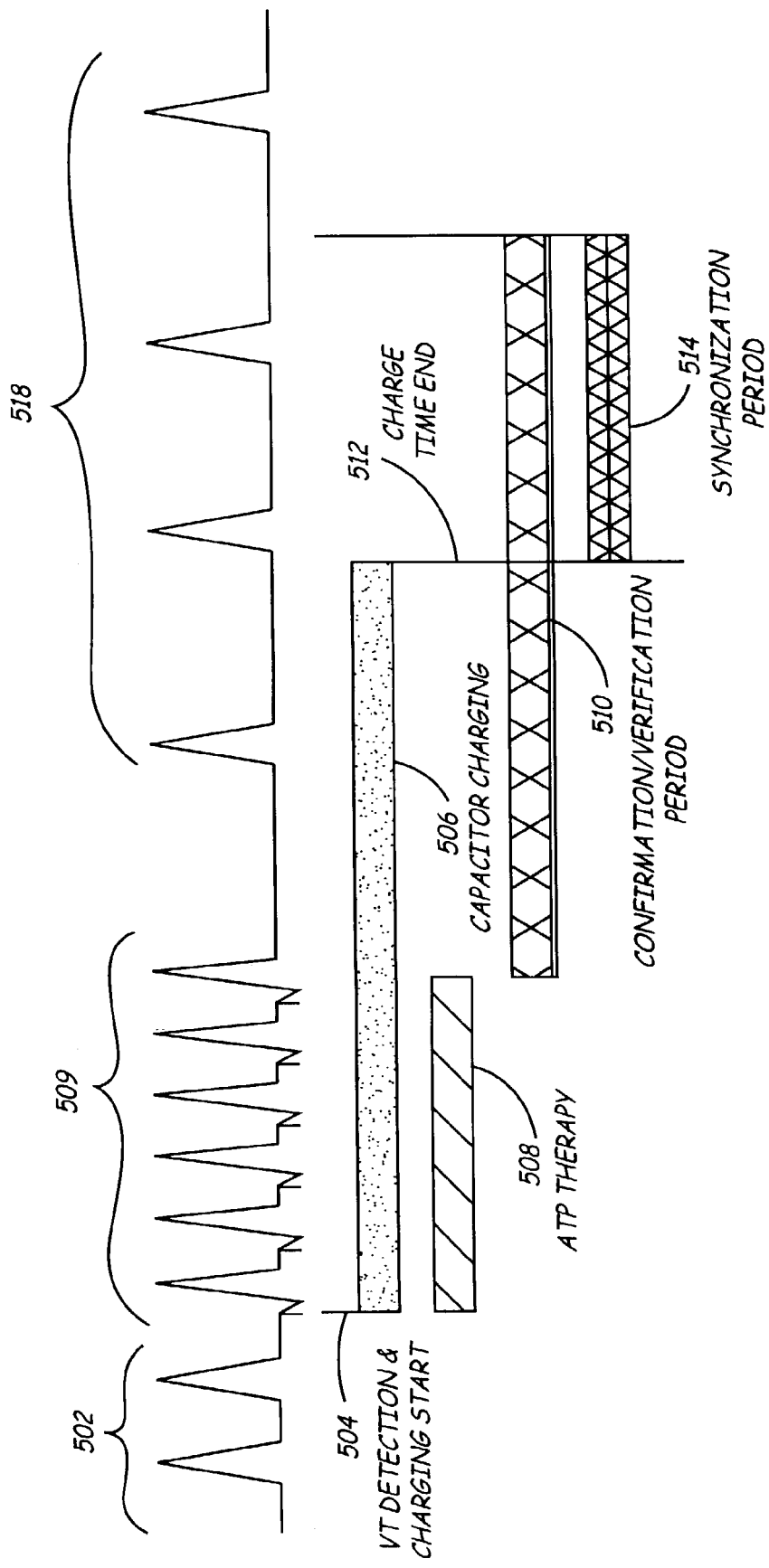
FIG. 6 is a simulated ECG strip along with timing periods illustrating an embodiment of the present invention wherein the ATP regimen terminated the tachycardia the ATP During Capacitor Charge mode of operation.

FIG. 6 is a simulated ECG illustrating a ventricular tachyarrhythmia and various timing periods showing that the ATP regimen was successful in terminating the tachyarrhythmia according to the present invention. In FIG. 6, time periods that are similar to those shown in FIG. 5 are labeled with like numeral designations. According to the embodiment of FIG. 6, the sequence of ATP pulses 509 is delivered during time period 508 as described above in response to detection of pulses 502 indicating the presence of a ventricular tachyarrhythmia. As with any of the embodiments of the invention discussed herein, this sequence might consist of burst, ramp, or ramp-plus pacing pulses, among others.

Confirmation/verification period 510 begins at the end of deliver of ATP pulses 509 upon expiration of time period 508, and ends upon detection of ventricular tachyarrhythmia termination where a transition to pulses 518 corresponding to a normal sinus rhythm occurs. Charging of capacitors ends either upon ventricular tachyarrhythmia termination or at charge-time end (CTE) 512, at which time shock delivery is aborted and the accumulated charge can be left on the capacitors or can be drained or dumped. Analysis of RCL as described above may be performed but is not required for decision making, i.e. delivery of or inhibiting the shock.

Figure 7:
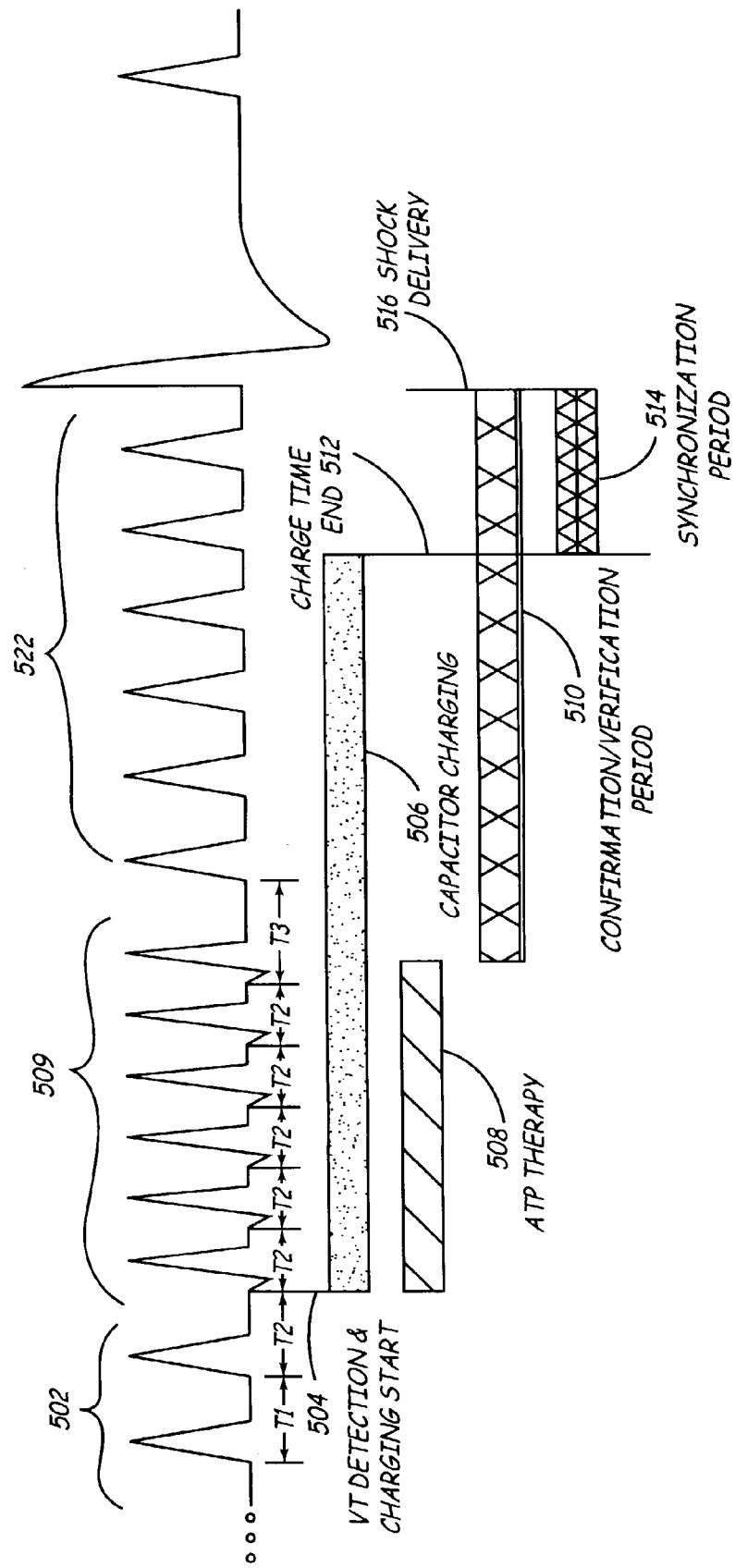
FIG. 7 is a simulated ECG strip along with timing periods illustrating an embodiment of the present invention wherein the RCL after the last ATP pulse was longer than the cut-off interval.

FIG. 7 is a simulated ECG illustrating a ventricular tachyarrhythmia and various timing periods showing that the ATP regimen was unsuccessful in terminating the tachyarrhythmia according to one embodiment of the present invention. As in FIGS. 5 and 6, ATP pulses 509 are delivered in FIG. 7 during time period 508 as described above in response to detection of a ventricular tachyarrhythmia 502. However, unlike in the illustration of FIG. 6, the ATP pulses 509 fail to terminate the ventricular tachyarrhythmia and the episode continues so that pulses 522 indicative of the ventricular tachyarrhythmia are detected during time confirmation/verification period 510. Once it is determined that the tachycardia has not been terminated, i.e., pulses 522 indicative of ventricular tachyarrhythmia are detected during confirmation/verification period 510, the return cycle length RCL, i.e., interval T3, is measured and the normalized return cycle length $RCL_N$ is computed, as described above. In the example illustrated by FIG. 7, the normalized return cycle length $RCL_N$ is less than the discrimination threshold interval $RCL_C$, similar to the description of FIG. 3A, and thus the present invention classified the tachyarrhythmia as ventricular tachycardia (VT). The synchronization period 514 begins following charge-time end 512, and culminates with shock delivery at time 516. If the ventricular tachyarrhythmia terminates during synchronization period 514, shock delivery is aborted and the accumulated charge on the capacitors would be retained for subsequent use, drained or dumped.

Figure 8:
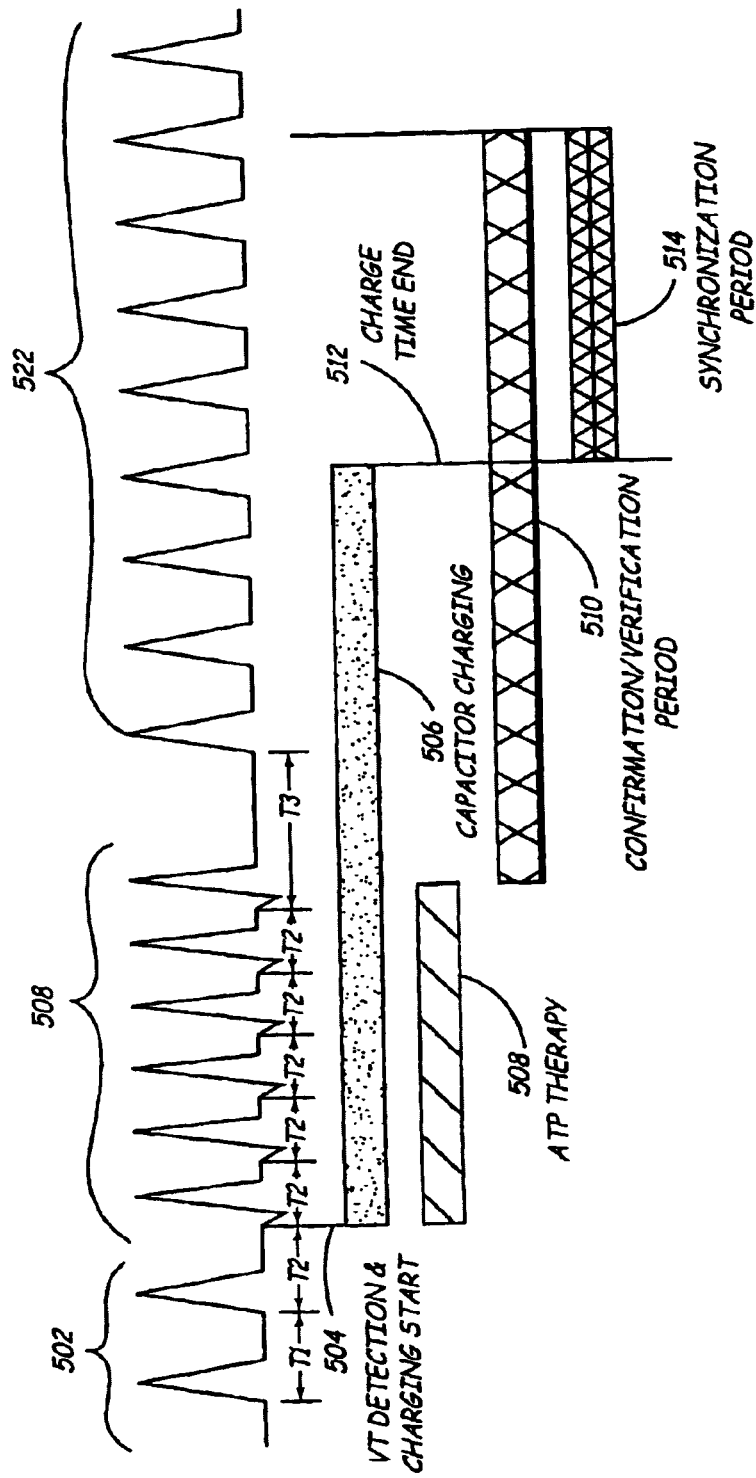
FIG. 8 is a simulated ECG strip along with timing periods illustrating an embodiment of the present invention wherein the RCL after the last ATP pulse was shorter than the cut-off interval.

In FIG. 8 as in FIG. 7 the episode continues during time 522. Again after the last ATP pulse the return cycle length T3 is measured and the normalized return cycle length $RCL_N$ is computed. In the example illustrated by FIG. 8, the normalized return cycle length $RCL_N$ is greater than the discrimination threshold interval $RCL_C$, similar to the description of FIG. 3B, and thus the present invention classifies the tachyarrhythmia as an (SVT). The shock therapy will be inhibited and the accumulated charge on the capacitors is retained for subsequent use, drained or dumped. Confirmation and synchronization periods may continue or be terminated since they are no longer required. If the pre-set therapy included options for treating SVTs, these therapies may be initiated. It is understood that, similar to FIGS. 3A and 3B, rather than using the normalized return cycle length $RCL_N$ to determine whether the intrinsic signal received subsequent to the last ATP pacing pulse corresponds to the cardiac event that was being addressed by the ATP pulse therapy, interval T3 could be compared to the discrimination threshold as described above.

The proposed methodology of the current invention can be used as a primary SVT/VT discriminator for single chamber ICDs. If after delivering the ATP regimen, the episode is found to be SVT, various actions may be initiated depending on the ICD system implanted. One such action for a single chamber ICD system with RV coil only may be to simply suspend subsequent ventricular therapies. Another action for a single chamber ICD system with RV and SVC coils would be to change the subsequent therapy to an atrial shock via SVC-can pathway. The amplitude of the shock can be made commensurate with requirements for terminating atrial arrhythmias (e.g. a 25 J shock via RV coil-can pathway may be replaced with a 5 J SVC-can shock). In addition, the timing of the shock can be adjusted to minimize patient discomfort (e.g., by delaying the shock until early morning so shock is delivered during sleep).

If the present invention is incorporated into single chamber ICDs with RV coil and pressure sensor, any subsequent ventricular therapies can be suspended for an episode classified as SVT only when the pressure is above an acceptable limit. Additionally, in single chamber ICDs with RV and SVC coils, and pressure sensor, any subsequent therapies can be delivered to the atrium if the episode is classified as SVT and if the pressure is above a threshold limit.

The proposed method can be used in dual chamber devices in conjunction with PR Logic to enhance overall specificity of SVT detection. This can be viewed as a compound discriminator in which PR Logic as disclosed in U.S. Pat. No. 5,545,186 issued to Olson et al Aug. 13, 1996, incorporated herein by reference in its entirety, may be used during initial detection and the present invention is used during redetection. The RCL discriminator is well suited for redetection because it uses only one beat. If an episode is found to be SVT during redetection in a dual chamber device, then ventricular therapy can be cancelled/suspended and atrial detection can be deployed to sub-classify the SVT episode into AT or AF, and to take appropriate therapeutic action.

The current invention is not limited for use in the ATP-DCC mode of ICDs but may also be employed in other ICD modes such as the antitachycardia pacing before capacitor charge (ATP-BCC) mode described in U.S. patent application Ser. No. 09/918,224 to DeGroot et al., filed Jul. 30, 2001, incorporated herein by reference in its entirety. Likewise the current invention is not limited for use in ICDs and antitachycardia pacemakers, but may be employed in various implanted medical devices. For example, if non-electrical and less painful atrial therapies are to be employed for SVT episodes, such as a drug pump to infuse drugs into the pericardial space, these therapies can be deployed after an episode is found to be SVT according to the present invention.

The RCL based discriminator described by the present invention is well suited for fast rhythms that physicians want to shock quickly. PR Logic is usually not applied to these rhythms because they are faster than the SVT Limit as disclosed in U.S. Pat. No. 5,545,186 referenced above. The RCL discriminator may be applied to tachyarrhythmias faster than the SVT Limit without significant deterioration in specificity and sensitivity of the methodology.

Figure 9:
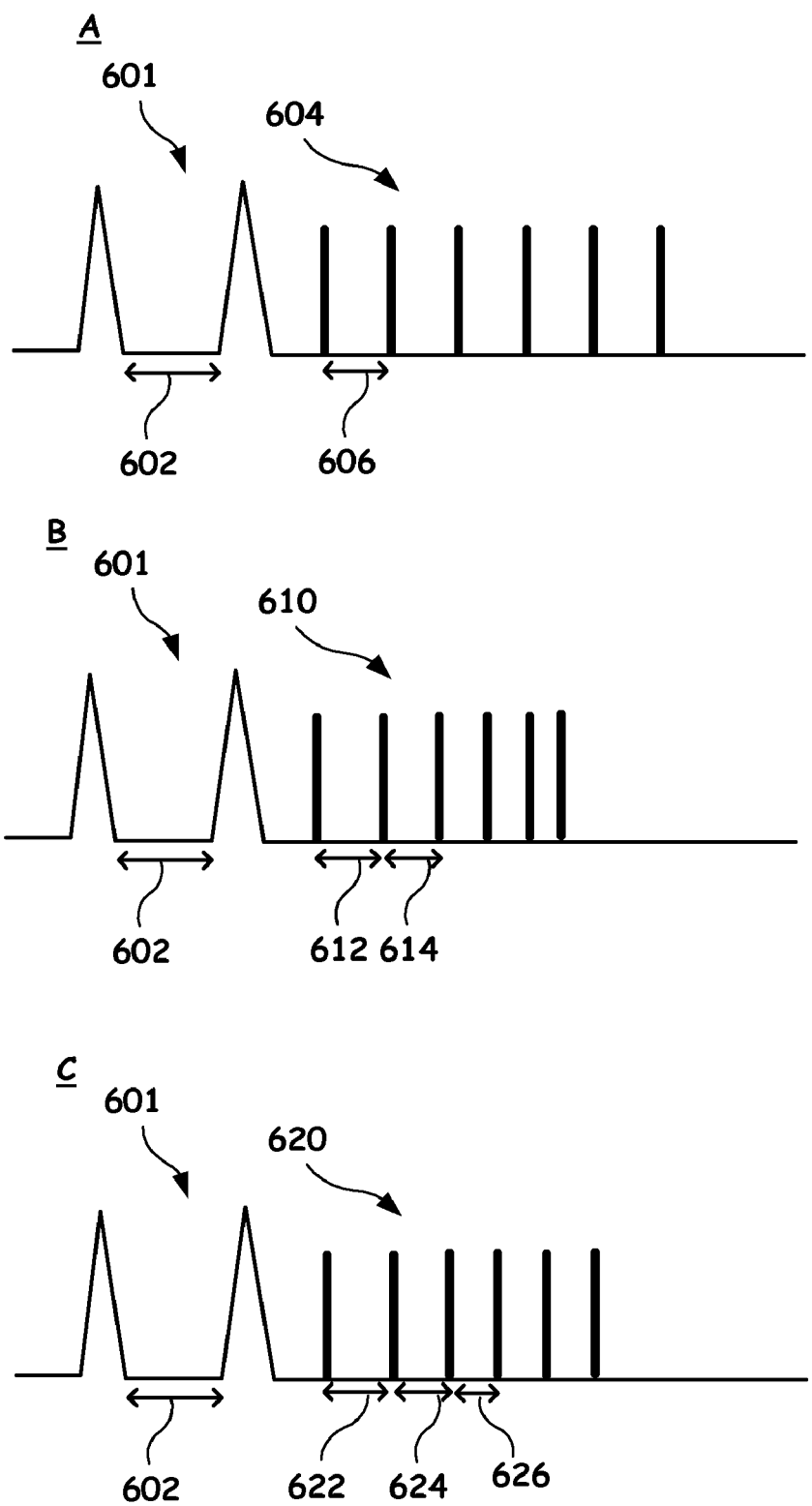
FIG. 9 is an illustration of burst, ramp, and ramp-plus ATP therapies.

FIG. 9 is an illustration of burst, ramp, and ramp-plus ATP therapies, any of which may be delivered during an ATP therapy time period 508 (shown in FIGS. 5, 6, and 7). In diagram A, pulses 601 correspond to detection of a ventricular tachyarrhythmia. A device, such as the ICD discussed above in reference to FIGS. 1 and 2, detects pulses 601 and starts the delivery of a burst ATP therapy 604. A burst ATP therapy 604 includes a programmed number of pacing pulses delivered at a constant pulse interval 606, which may be computed to be a programmed percentage of the detected tachyarrhythmia pulse interval 602.

In diagram B, a ramp ATP therapy 610 is delivered following detection of tachyarrhythmia pulses 601. Ramp ATP therapy 610 includes a programmed number of pacing pulses delivered at a progressively decreasing pulse interval based on a previously programmed interval decrement. The first pulse interval 612 is set as a percentage of the detected tachyarrhythmia pulse interval 602. The next pulse interval 614 is set equal to the first pulse interval 612 less the interval decrement. Each successive pulse is delivered at a time interval equal to the previous time interval less the interval decrement.

In diagram C, a ramp-plus ATP therapy 620 is delivered following detection of tachyarrhythmia pulses 601. The ramp-plus ATP therapy 620 includes a programmed number of pulses wherein the first pulse interval 622 is set as a first percentage of the detected tachyarrhythmia pulse interval 602. The second pulse interval 624 is set according to a second percentage of the detected tachyarrhythmia pulse interval 602, and all remaining pulse intervals 626 are set according to a third percentage of the detected tachyarrhythmia pulse interval.

The preceding specific embodiments are illustrative of the practice of the invention. It is to be understood, therefore, that other expedients known to those of skill in the art or disclosed herein may be employed without departing from the invention or the scope of the appended claims. It is therefore to be understood that the invention may be practiced otherwise than is specifically described, without departing from the scope of the present invention. As to every element, it may be replaced by anyone of infinite equivalent alternatives, only some of which are disclosed in the specification.

The present invention is described herein in an embodiment that includes an implantable cardioverter defibrillator (ICD). Those of ordinary skill in the art, however, with the benefit of the present disclosure will appreciate that the present invention may be advantageously practiced in connection with numerous other types of implanted medical devices (IMDs) such as pacemakers, neurostimulators, and the like. Detailed embodiments described above are intended to be exemplary of the concepts of the present invention and should not be considered limiting with regard to the following claims.

What is claimed is:

1. An apparatus for discriminating between cardiac events, comprising:
an input circuit for receiving signals indicative of the cardiac events;
a first output circuit for generating pulses in response to the received signals; and
a microprocessor for determining whether a signal received by the input circuit subsequent to the generated pacing pulses corresponds to a first predetermined cardiac event in response to an elapsed time period (T3) between the generated pulses and the subsequently received signal and a predetermined discrimination threshold (T4).

2. The apparatus of claim 1, wherein the microprocessor is programmed to determined that the signal received by the input circuit subsequent to the generated pacing pulses corresponds to the first predetermined cardiac event in response to the elapsed time period (T3) between the generated pulses and the subsequently received signal being less than the predetermined discrimination threshold (T4) and wherein the microprocessor is programmed to permit subsequent scheduled delivery of a therapy in response to the signal received by the input circuit subsequent to the generated pacing pulses corresponding to the first predetermined cardiac event.

3. The apparatus of claim 1, wherein the microprocessor is programmed to determined that the signal received by the input circuit subsequent to the generated pacing pulses does not correspond to the first predetermined cardiac event in response to the elapsed time period (T3) between the generated pulses and the subsequently received signal being greater than or equal to the predetermined discrimination threshold (T4), and the microprocessor is programmed inhibit subsequent scheduled delivery of a therapy in response to the signal received by the input circuit subsequent to the generated pacing pulses not corresponding to the first predetermined cardiac event.

4. The apparatus of claim 1, further comprising a second output circuit for delivering shock therapy, wherein the first output circuit generates the pulses during charging of the second output circuit.

5. The apparatus of claim 1, further comprising a second output circuit for delivering shock therapy, wherein the first output circuit generates the pulses prior to charging of the second output circuit.

6. The apparatus of claim 1, wherein the first output circuit generates the pulses in response to the input circuit receiving consecutive signals, separated by a predetermined time period (T1), corresponding to a rate of the first predetermined cardiac event, and wherein the elapsed time period (T3) is normalized to the predetermined time period (T1).

7. The apparatus of claim 1, wherein the first output circuit generates the pulses in response to the input circuit receiving consecutive signals, separated by a predetermined time period (T1), corresponding to a rate of the first predetermined cardiac event, and wherein the predetermined discrimination threshold (T4) is a percentage of the predetermined time period (T1).

8. The apparatus of claim 7, wherein the predetermined discrimination threshold (T4) corresponds to approximately 190% of the predetermined time period (T1).

9. The apparatus of claim 1, wherein the pulses generated by the first output circuit correspond to anti-tachycardia pacing pulses.

10. The apparatus of claim 1, wherein the pulses generated by the first output circuit include a first pulse and a last pulse, and wherein the elapsed time period (T3) extends between the last pulse and the subsequently received signal.

11. The apparatus of claim 1, wherein the microprocessor is programmed to determined that the signal received by the input circuit subsequent to the generated pacing pulses corresponds to the first predetermined cardiac event in response to the elapsed time period (T3) between the generated pulses and the subsequently received signal being less than the predetermined discrimination threshold (T4) and wherein the microprocessor is programmed to permit subsequent scheduled delivery of a therapy in response to the signal received by the input circuit subsequent to the generated pacing pulses corresponding to the first predetermined cardiac event, and wherein the microprocessor is programmed to determine that the signal received by the input circuit subsequent to the generated pacing pulses corresponds to a second predetermined cardiac event in response to the elapsed time period (T3) between the generated pulses and the subsequently received signal being greater than or equal to the predetermined discrimination threshold (T4) and is programmed to inhibit subsequent scheduled delivery of the therapy for the first predetermined cardiac event in response to the signal received by the input circuit subsequent to the generated pacing pulses corresponding to the second predetermined cardiac event.

12. The apparatus of claim 11, wherein the microprocessor is programmed to initiate a therapy corresponding to the second predetermined cardiac event in response to determining that the signal received by the input circuit subsequent to the generated pacing pulses corresponds to the second predetermined cardiac event.

13. The apparatus of claim 1, wherein the first predetermined cardiac event is a ventricular tachycardia and a second predetermined cardiac event is a supraventricular tachycardia, and wherein the microprocessor is programmed to determine that the subsequently received signal corresponds to the supraventricular tachycardia in response to the elapsed time period (T3) being greater than or equal to the predetermined discrimination threshold (T4) and that the subsequently received signal corresponds to the ventricular tachycardia in response to the elapsed time period (T3) being less than the predetermined discrimination threshold (T4).

14. The apparatus of claim 13, wherein the microprocessor initiates a supraventricular tachycardia therapy in response to determining that the subsequently received signal corresponds to the supraventricular tachycardia.

15. The apparatus of claim 1, wherein the pulses generated by the first output circuit are separated by a predetermined interval (T2) that is a function of the predetermined time period (T1).

16. The apparatus of claim 10, wherein the pulses generated by the first output circuit are one of burst pulses, ramp pulses and ramp-plus pacing pulses.

17. An apparatus for discriminating between cardiac events, comprising:
an input circuit for receiving signals indicative of the cardiac events;
a first output circuit for generating pulses in response to the input circuit receiving consecutive signals, separated by a predetermined time period (T1), corresponding to a rate of a first predetermined cardiac event; and
a microprocessor for determining whether a signal received by the input circuit subsequent to the generated pacing pulses corresponds to the first predetermined cardiac event in response to an elapsed time period (T3) between the generated pulses and the subsequently received signal and a predetermined discrimination threshold (T4).

18. The apparatus of claim 17, wherein the microprocessor is programmed to determine that the signal received by the input circuit subsequent to the generated pacing pulses corresponds to the first predetermined cardiac event in response to the elapsed time period (T3) between the generated pulses and the subsequently received signal being less than the predetermined discrimination threshold (T4) and wherein the microprocessor is programmed to permit subsequent scheduled delivery of a therapy in response to the signal received by the input circuit subsequent to the generated pacing pulses corresponding to the first predetermined cardiac event.

19. The apparatus of claim 17, wherein the microprocessor is programmed to determine that the signal received by the input circuit subsequent to the generated pacing pulses does not correspond to the first predetermined cardiac event in response to the elapsed time period (T3) between the generated pulses and the subsequently received signal being greater than or equal to the predetermined discrimination threshold (T4) and wherein the microprocessor is programmed to permit subsequent scheduled delivery of a therapy in response to the signal received by the input circuit subsequent to the generated pacing pulses not corresponding to the first predetermined cardiac event.

20. The apparatus of claim 17, further comprising a second output circuit for delivering shock therapy, wherein the first output circuit generates the pulses during charging of the second output circuit.

21. The apparatus of claim 17, further comprising a second output circuit for delivering shock therapy, wherein the first output circuit generates the pulses prior to charging of the second output circuit.

22. The apparatus of claim 17, wherein the microprocessor is programmed to determine that the signal received by the input circuit subsequent to the generated pacing pulses corresponds to the first predetermined cardiac event in response to the elapsed time period (T3) between the generated pulses and the subsequently received signal being less than the predetermined discrimination threshold (T4) and wherein the microprocessor is programmed to permit subsequent scheduled delivery of a therapy in response to the signal received by the input circuit subsequent to the generated pacing pulses corresponding to the first predetermined cardiac event, and wherein the microprocessor is programmed to determine that the signal received by the input circuit subsequent to the generated pacing pulses corresponds to a second predetermined cardiac event in response to the elapsed time period (T3) between the generated pulses and the subsequently received signal being greater than or equal to the predetermined discrimination threshold (T4) and wherein the microprocessor is programmed to inhibit subsequent scheduled delivery of the therapy for the first predetermined cardiac event in response to the signal received by the input circuit subsequent to the generated pacing pulses corresponding to the second predetermined cardiac event.

23. The apparatus of claim 22, wherein the microprocessor is programmed to initiate a therapy corresponding to the second predetermined cardiac event in response to the determining that the signal received by the input circuit subsequent to the generated pacing pulses corresponds to the second predetermined cardiac event.

24. The apparatus of claim 17, wherein the first predetermined cardiac event is a ventricular tachycardia and a second predetermined cardiac event is a supraventricular tachycardia, and wherein the microprocessor determines that the subsequently received signal corresponds to the supraventricular tachycardia in response to the elapsed time period (T3) being greater than or equal to the predetermined discrimination threshold (T4).

25. The apparatus of claim 24, wherein the microprocessor is programmed to initiate a supraventricular tachycardia therapy in response to determining that the subsequently received signal corresponds to the supraventricular tachycardia.

26. The apparatus of claim 17, wherein the elapsed time period (T3) is normalized to the predetermined time period (T1).

27. The apparatus of claim 26, wherein the predetermined discrimination threshold (T4) corresponds to approximately 190% of the predetermined time period (T1).

28. The apparatus of claim 27, wherein the pulses generated by the first output circuit correspond to anti-tachycardia pacing pulses.

29. The apparatus of claim 27, wherein the pulses generated by the first output circuit include a first pulse and a last pulse, and wherein the elapsed time period (T3) extends between the last pulse and the subsequently received signal.

30. The apparatus of claim 27, wherein the pulses generated by the first output circuit are separated by a predetermined interval (T2) that is a function of the predetermined time period (T1).

31. The apparatus of claim 27, wherein the pulses generated by the first output circuit are one of burst pulses, ramp pulses and ramp-plus pacing pulses.

32. A method of discriminating between cardiac events, comprising:
receiving signals indicative of the cardiac events by an input circuit;
generating pulses in response to the received signals; and
determining that a signal received by the input circuit subsequent to the generated pacing pulses corresponds to a first predetermined cardiac event in response to an elapsed time period (T3) between the generated pulses and the subsequently received signal and a predetermined discrimination threshold (T4).

33. The method of claim 32, wherein the step of determining further comprises determining that the signal received by the input circuit subsequent to the generated pacing pulses corresponds to the first predetermined cardiac event in response to the elapsed time period (T3) between the generated pulses and the subsequently received signal being less than the predetermined discrimination threshold (T4), and permitting subsequent scheduled delivery of a therapy in response to the signal received by the input circuit subsequent to the generated pacing pulses corresponding to the first predetermined cardiac event.

34. The method of claim 32, wherein the step of determining further comprises determining that the signal received by the input circuit subsequent to the generated pacing pulses does not correspond to the first predetermined cardiac event in response to the elapsed time period (T3) between the generated pulses and the subsequently received signal being greater than or equal to the predetermined discrimination threshold (T4), and inhibiting subsequent scheduled delivery of a therapy in response to the signal received by the input circuit subsequent to the generated pacing pulses not corresponding to the first predetermined cardiac event.

35. The method of claim 32, further comprising charging an output circuit for delivering shock therapy in response to detection of the first cardiac event, wherein the pulses are generated during charging of the output circuit.

36. The method of claim 32, further comprising charging an output circuit for delivering shock therapy in response to detection of the first cardiac event, wherein the pulses are generated prior to charging of the output circuit.

37. The method of claim 32, wherein the pulses are generated in response to receipt of consecutive signals, separated by a predetermined time period (T1), corresponding to a rate of the first predetermined cardiac event, and wherein the elapsed time period (T3) is normalized to the predetermined time period (T1).

38. The method of claim 32, wherein the pulses are generated in response to receipt of consecutive signals, separated by a predetermined time period (T1), corresponding to a rate of the predetermined cardiac event, and wherein the predetermined discrimination threshold (T4) is a percentage of the predetermined time period (T1).

39. The method of claim 32, wherein the predetermined discrimination threshold (T4) corresponds to approximately 190% of the predetermined time period (T1).

40. The method of claim 32, the step of determining further comprising determining that the signal received subsequent to the generated pacing pulses corresponds to the first predetermined cardiac event in response to the elapsed time period (T3) between the generated pulses and the subsequently received signal being less than the predetermined discrimination threshold (T4), permitting subsequent scheduled delivery of a therapy in response to the signal received subsequent to the generated pacing pulses corresponding to the first predetermined cardiac event, determining that the signal received by the input circuit subsequent to the generated pacing pulses corresponds to a second predetermined cardiac event in response to the elapsed time period (T3) between the generated pulses and the subsequently received signal being greater than or equal to the predetermined discrimination threshold (T4), and inhibiting subsequent scheduled delivery of the therapy for the first predetermined cardiac event in response to the signal received by the input circuit subsequent to the generated pacing pulses corresponding to a second predetermined cardiac event.

41. The method of claim 40, further comprising initiating a therapy corresponding to the second predetermined cardiac event in response to the determining that the signal received by the input circuit subsequent to the generated pacing pulses corresponds to the second predetermined cardiac event.

42. The method of claim 32, wherein the pulses are generated in response to receipt of consecutive signals, separated by a predetermined time period (T1), corresponding to the rate of the first predetermined cardiac event, and wherein the pulses are separated by a predetermined interval (T2) that is a function of the predetermined time period (T1).

* * * * *

UNITED STATES PATENT AND TRADEMARK OFFICE
CERTIFICATE OF CORRECTION

PATENT NO.         : 7,149,577 B2                                            Page 1 of 1
APPLICATION NO.  : 10/307687
DATED              : December 12, 2006
INVENTOR(S)        : Sharma et al.

It is certified that error appears in the above-identified patent and that said Letters Patent is hereby corrected as shown below:

Column 17, line 49, please delete "(T4)," and insert --(T4)--

Column 17, line 49, please delete "and the" and insert --and wherein the--

Column 18, line 36, please delete "and is" and insert --and wherein the microprocessor is--

Column 18, line 61, please delete "initiates a" and insert --is programmed to initiate a--

Signed and Sealed this

Fifth Day of June, 2007

JON W. DUDAS
*Director of the United States Patent and Trademark Office*